United States Patent
Cai

(10) Patent No.: US 11,173,301 B2
(45) Date of Patent: Nov. 16, 2021

(54) METHOD AND DEVICE FOR ASSISTING RESPIRATION BY ELECTRICAL STIMULATION

(71) Applicant: YAGUO INC., Beijing (CN)

(72) Inventor: Xiaoqi Cai, Beijing (CN)

(73) Assignee: YAGUO INC., Beijing (CN)

( * ) Notice: Subject to any disclaimer, the term of this patent is extended or adjusted under 35 U.S.C. 154(b) by 408 days.

(21) Appl. No.: 16/325,009

(22) PCT Filed: Aug. 31, 2017

(86) PCT No.: PCT/CN2017/099854
§ 371 (c)(1),
(2) Date: Apr. 24, 2019

(87) PCT Pub. No.: WO2018/028719
PCT Pub. Date: Feb. 15, 2018

(65) Prior Publication Data
US 2021/0244946 A1 Aug. 12, 2021

(30) Foreign Application Priority Data

Aug. 12, 2016 (CN) .......................... 201610662131.5
Aug. 12, 2016 (CN) .......................... 201620871179.2

(51) Int. Cl.
*A61N 1/36* (2006.01)
(52) U.S. Cl.
CPC ....... *A61N 1/3601* (2013.01); *A61N 1/36034* (2017.08)

(58) Field of Classification Search
CPC .................. A61N 1/3601; A61N 1/36034; A61N 1/3611; A61B 5/0816; A61B 5/08; A61B 5/087
See application file for complete search history.

(56) References Cited

U.S. PATENT DOCUMENTS 2,821,189 A * 1/1958 Hofmann ............. A61N 1/3601
601/41
9,776,005 B2 10/2017 Meyyappan et al.
(Continued)

FOREIGN PATENT DOCUMENTS

CN 1085457 A 4/1994
CN 104684614 A 6/2015
(Continued)

OTHER PUBLICATIONS

English translation of the Office Action dated Feb. 23, 2019 for Chinese Application No. 201610662131.5.
(Continued)

Primary Examiner — Tammie K Marlen
(74) Attorney, Agent, or Firm — David D. Brush; Westman, Champlin & Koehler, P.A.

(57) ABSTRACT

A method for assisting respiration by electrical stimulation includes: acquiring a time parameter of a target respiratory process; and outputting a phrenic nerve stimulating signal to a diaphragm stimulating electrode within a time period corresponding to inspiration and outputting an abdominal muscle stimulating signal to an abdominal muscle stimulating electrode within a time period corresponding to expiration, according to the time parameter of the target respiratory process.

9 Claims, 2 Drawing Sheets

---

101 — acquiring a time parameter of a target respiratory process

102 — outputting a phrenic nerve stimulating signal to a diaphragm stimulating electrode within a time period corresponding to inspiration and outputting an abdominal muscle stimulating signal to an abdominal muscle stimulating electrode within a time period corresponding to expiration, according to the time parameter of the target respiratory process

(56) References Cited

U.S. PATENT DOCUMENTS

2016/0287877 A1* 10/2016 Jung .................... A61N 1/3611
2018/0008826 A1* 1/2018 Dimarco ............ A61N 1/36171

FOREIGN PATENT DOCUMENTS

| CN | 104939815 A | 9/2015 |
|---|---|---|
| CN | 106215319 A | 12/2016 |
| CN | 206275918 U | 6/2017 |

OTHER PUBLICATIONS

Office Action dated Feb. 23, 2019 for Chinese Application No. 201610662131.5.
English translation of the International Search Report dated Oct. 16, 2017 for corresponding International Application No. PCT/CN2017/099854, filed Aug. 31, 2017.
English translation of the International Written Opinion dated Oct. 127, 2017 for corresponding International Application No. PCT/CN2017/099854, filed Aug. 31, 2017.

\* cited by examiner

METHOD AND DEVICE FOR ASSISTING RESPIRATION BY ELECTRICAL STIMULATION

CROSS-REFERENCE TO RELATED APPLICATIONS

This application is a Section 371 National Stage Application of International Application No. PCT/CN2017/099854, filed Aug. 31, 2017, the content of which is incorporated herein by reference in its entirety, and published as WO 2018/028719 on Feb. 15, 2018, not in English.

This application claims priority to Chinese Patent Application Serial No. 201610662131.5, filed with the State Intellectual Property Office of P. R. China by CAI, Xiaoqi on Aug. 12, 2016 under the title of METHOD AND APPARATUS FOR ASSISTING RESPIRATION BY ELECTRICAL STIMULATION, which is hereby incorporated by reference in its entirety.

This application claims priority to Chinese Patent Application Serial No. 201620871179.2, filed with the State Intellectual Property Office of P. R. China by YAGUO INC. on Aug. 12, 2016 under the title of APPARATUS FOR ASSISTING RESPIRATION BY ELECTRICAL STIMULATION, which is hereby incorporated by reference in its entirety.

FIELD

The present disclosure relates to medical apparatuses and instruments, and more particularly to a method and apparatus for assisting respiration by electrical stimulation.

BACKGROUND

With the development of electronic technology, functional electrical stimulation technologies have been widely used because they may replace or correct functions that have been lost by limbs and organs. External diaphragm pacemaker, as one of the most commonly used electrical stimulation apparatuses for respiratory therapy, induces diaphragmatic contraction by electrical stimulation, thereby increasing inspiratory tidal volume and enhancing motion intensity of the diaphragm. On the other hand, training a patient to recover a spontaneous breathing ability by applying the electrical stimulation on abdominal muscles to exercise respiratory muscles has also become a new idea of the respiratory therapy. Although synergistic electrical stimulations on the diaphragm and the abdominal muscle are undoubtedly more conducive to the recovery of the patient's spontaneous breathing ability, there are still few products adopting this idea at present. The key and difficult point in implementation of the synergistic electrical stimulations on the diaphragm and the abdominal muscle is that the electrical stimulations on the diaphragm and the abdominal muscle not only need to be coordinated with each other, but also need to be synchronized with patient's respiration. Therefore, how to coordinate the electrical stimulations on the diaphragm and the abdominal muscle to achieve the synchronization with user's respiration has become an urgent technical problem to be solved in the art.

SUMMARY

Embodiments of the present disclosure provide a method and apparatus for assisting respiration by electrical stimulation, which are able to coordinate electrical stimulations on diaphragm and abdominal muscle to achieve synchronization with user's respiration.

In a first aspect, embodiments of the present disclosure provide a method for assisting respiration by electrical stimulation, including: acquiring a time parameter of a target respiratory process; and outputting a phrenic nerve stimulating signal to a diaphragm stimulating electrode within a time period corresponding to inspiration and outputting an abdominal muscle stimulating signal to an abdominal muscle stimulating electrode within a time period corresponding to expiration, according to the time parameter of the target respiratory process.

In the method for assisting respiration by electrical stimulation according to an embodiment of the present disclosure, acquiring a time parameter of a target respiratory process specifically includes: continuously receiving instruction messages at a respiratory synchronization port; and determining the time parameter of the target respiratory process according to an inspiration starting identifier, an inspiration ending identifier, an expiration starting identifier or an expiration ending identifier included in each instruction message and a receipt time of each instruction message.

In the method for assisting respiration by electrical stimulation according to an embodiment of the present disclosure, acquiring a time parameter of a target respiratory process further includes: acquiring the time parameter of the target respiratory process from pre-stored configuration data when the time parameter of the target respiratory process is un-obtainable from the instruction message.

In the method for assisting respiration by electrical stimulation according to an embodiment of the present disclosure, the phrenic nerve stimulating signal and/or the abdominal muscle stimulating signal are/is generated by a current source circuit controlled by a digital signal.

The method for assisting respiration by electrical stimulation according to an embodiment of the present disclosure further includes: detecting an output current of the phrenic nerve stimulating signal and/or that of the abdominal muscle stimulating signal; and generating an electrode detaching indication signal when the output current of the phrenic nerve stimulating signal and/or that of the abdominal muscle stimulating signal are/is lower than a preset value.

In a second aspect, embodiments of the present disclosure further provide an apparatus for assisting respiration by electrical stimulation, including: an acquiring module, configured to acquire a time parameter of a target respiratory process; and an outputting module, configured to output a phrenic nerve stimulating signal to a diaphragm stimulating electrode within a time period corresponding to inspiration and output an abdominal muscle stimulating signal to an abdominal muscle stimulating electrode within a time period corresponding to expiration, according to the time parameter of the target respiratory process acquired by the acquiring module.

In the apparatus for assisting respiration by electrical stimulation according to an embodiment of the present disclosure, the acquiring module specifically includes: a receiving unit, configured to continuously receive instruction messages at a respiratory synchronization port; and a determining unit, configured to determine the time parameter of the target respiratory process according to an inspiration starting identifier, an inspiration ending identifier, an expiration starting identifier or an expiration ending identifier included in each instruction message and a receipt time of each instruction message.

In the apparatus for assisting respiration by electrical stimulation according to an embodiment of the present disclosure, the acquiring module further includes: an acquiring unit, configured to acquire the time parameter of the target respiratory process from pre-stored configuration data when the time parameter of the target respiratory process is un-obtainable from the instruction message.

In the apparatus for assisting respiration by electrical stimulation according to an embodiment of the present disclosure, the outputting module includes a current source circuit controlled by a digital signal and configured to generate the phrenic nerve stimulating signal and/or the abdominal muscle stimulating signal.

The apparatus for assisting respiration by electrical stimulation according to an embodiment of the present disclosure further includes: a detecting module, configured to detect an output current of the phrenic nerve stimulating signal and/or that of the abdominal muscle stimulating signal and generate an electrode detaching indication signal when the output current of the phrenic nerve stimulating signal and/or that of the abdominal muscle stimulating signal are/is lower than a preset value.

Another objective of embodiments of the present disclosure is to provide a device, including: one or more processors; a memory; and one or more procedures stored in the memory, wherein the one or more procedures, when executed by the one or more processors, cause the one or more processors to perform the method for assisting respiration by electrical stimulation as described in embodiments hereinbefore.

Yet another objective of embodiments of the present disclosure is to provide a nonvolatile computer storage medium having stored therein one or more procedures that, when executed by a device, cause the device to perform the method for assisting respiration by electrical stimulation as described in embodiments hereinbefore.

BRIEF DESCRIPTION OF THE DRAWINGS

In order to illustrate embodiments of the present disclosure more clearly, drawings to be used in the description of the embodiments of the present disclosure or the related art will be briefly described below. It is evident that the drawings in the following description are only some embodiments of the present disclosure, and other drawings may be obtained by those skilled in the art based on these drawings without any inventive labor.

DETAILED DESCRIPTION

Figure 1:
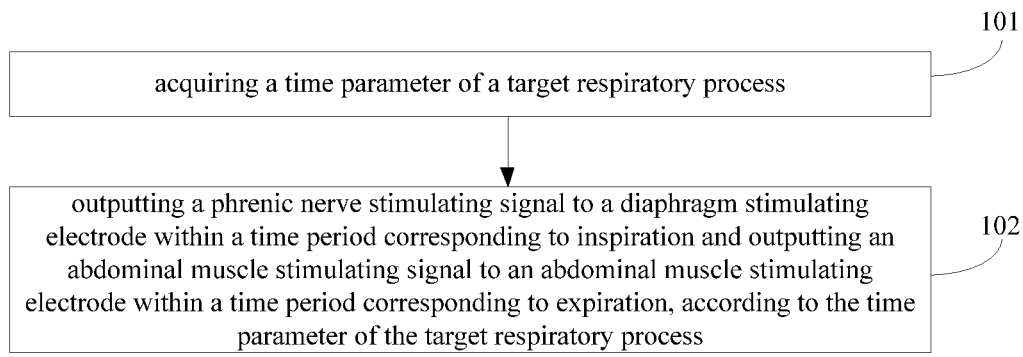
FIG. 1 is a flow chart of a method for assisting respiration by electrical stimulation according to an embodiment of the present disclosure.

Embodiments of the present disclosure will be described in detail below, examples of which are shown in the accompanying drawings, in which the same or similar elements and elements having same or similar functions are denoted by like reference numerals throughout the descriptions. The embodiments described below with reference to the accompanying drawings are explanatory and illustrative, which are used to generally understand the present disclosure, and shall not be construed to limit the present disclosure.

Referring to the following descriptions and drawings, these and other aspects of the embodiments of the present disclosure will be apparent. In these descriptions and drawings, some specific approaches of the embodiments of the present disclosure are provided, so as to show some ways to perform the principle of the embodiments of the present disclosure, however it should be understood that the embodiment of the present disclosure is not limited thereby. Instead, the embodiments of the present disclosure comprise all the variants, modifications and their equivalents within the spirit and scope of the appended claims.

In the following, some embodiments of the present disclosure will be described with reference to drawings.

FIG. 1 is a flow chart of a method for assisting respiration by electrical stimulation according to an embodiment of the present disclosure. Referring to FIG. 1, the method for assisting respiration by electrical stimulation includes:

step 101: acquiring a time parameter of a target respiratory process; and step 102: outputting a phrenic nerve stimulating signal to a diaphragm stimulating electrode within a time period corresponding to inspiration and outputting an abdominal muscle stimulating signal to an abdominal muscle stimulating electrode within a time period corresponding to expiration, according to the time parameter of the target respiratory process.

It should be illustrated that, although an implementation where the step 101 is performed before the step 102 is illustrated as an example in FIG. 1, in other implementations of the present invention, there is no clear sequence between the operations described at step 101 and step 102.

It should be illustrated that, the method for assisting respiration by electrical stimulation according to the embodiments of the present disclosure may be applied to any medical apparatus and instrument having a respiratory assisting function, such as a respirator, an external pacemaker, a respiratory rehabilitation therapeutic instrument, etc.

It is to be understood that, as an example of effects of outputting the phrenic nerve stimulating signal to the diaphragm stimulating electrode within the time period corresponding to the inspiration, user's diaphragm may contract under the stimulation of the phrenic nerve stimulating signal of the diaphragm stimulating electrode, thereby increasing the user's inspiratory tidal volume. As an example of effects of outputting the abdominal muscle stimulating signal to the abdominal muscle stimulating electrode within the time period corresponding to the expiration, user's abdominal muscle may contract under the stimulation of the abdominal muscle stimulating signal of the abdominal muscle stimulating electrode, thereby increasing peak expiratory flow or peak cough flow.

It can be seen that, in the method according to embodiments of the present disclosure, based on the acquisition of the time parameter of the target respiratory process, the electrical stimulations are respectively applied to the diaphragm and the abdominal muscle in accordance with the target respiratory process, thereby making the electrical stimulations on the diaphragm and the abdominal muscle coordinated with each other. Under the case that the target respiratory process sufficiently matches an actual respiratory process, the method according to embodiments of the present disclosure is able to achieve the respiratory assisting electrical stimulation highly synchronized with user's respiratory process, which is not only more beneficial to improving user's spontaneous breathing ability and coughing ability, but also beneficial to increasing the comfortable sensation of the user.

In the above step 101, it is to be understood that, in order to assist respiration by electrical stimulation, it needs to synchronize the electrical stimulation with the actual respiratory process. Therefore, in order to determine a timing sequence of electrical stimulation signals, it needs to determine the time parameter of the target respiratory process from the target respiratory process before the application of the electrical stimulation, i.e., the time parameter of the target respiratory process specifically refers to a parameter for determining the timing sequence of the electrical stimulation signal. Specifically, the time parameter of the target respiratory process acquired at any time may include any one or more of a start time of a first inspiration, a start time of a first expiration, a start time of a next inspiration, a start time of a next expiration, an end time of the current inspiration, an end time of the current expiration, as well as a respiratory cycle, a respiratory frequency, an inspiratory duration, an end-inspiratory pause duration, and an expiratory duration when the target respiratory process is periodic, which may be selected by those skilled in the art according to actual needs (it is unnecessary to include all the parameters with a conversion relationship). As an example for the selection with a minimum requirement, the time parameter acquired when the phrenic nerve stimulating signal or the abdominal muscle stimulating signal is not output should be at least sufficient to determine a start time of the next phrenic nerve stimulating signal or abdominal muscle stimulating signal to be output, while the time parameter acquired when the phrenic nerve stimulating signal or the abdominal muscle stimulating signal is being output should be at least sufficient to determine an end time of the current output phrenic nerve stimulating signal or abdominal muscle stimulating signal.

It is also to be understood that, after the desired time parameter of the target respiratory process is acquired at any time, at least the start time of the phrenic nerve stimulating signal or the abdominal muscle stimulating signal to be output or the end time of the phrenic nerve stimulating signal or the abdominal muscle stimulating signal being outputted can be determined, such that the method according to embodiments of the present disclosure is able to apply the electrical stimulations in harmony with the actual respiratory process in a configured manner. Of course, the time parameter of the target respiratory process may be derived from pre-stored configuration data or from an electrical signal collected from the actual respiratory process.

As a specific example where the time parameter of the target respiratory process is derived from the pre-stored configuration data, the above step 101 may specifically include the following processes: pre-configuring the target respiratory process as a periodic respiratory process, and acquiring the time parameter thereof, specifically including: the inspiratory duration (0.5 to 5 s), the end-inspiratory pause duration (0 to 2 s), the expiratory duration (0.5 to 5 s), the respiratory frequency (2-25 times per minute), an electrical stimulation duration (1-30 min) and a start time (determined by a key action of the user). Thereby, the above step 102 specifically includes the following processes: outputting the phrenic nerve stimulating signal (a current signal) to the diaphragm stimulating electrode at a start time, in which the specific parameter of the phrenic nerve stimulating signal may be pre-configured, including a current intensity ranging from 0 to 100 mA, a pulse frequency ranging from 20 to 100 Hz, or a pulse width ranging from 100 to 500 us; stopping outputting the phrenic nerve stimulating signal to the diaphragm stimulating electrode after an inspiratory duration (0.5 to 5 s) from the start time; stating outputting the abdominal muscle stimulating signal to the abdominal muscle stimulating electrode after an end-inspiratory pause duration (0 to 2 s); stopping outputting the abdominal muscle stimulating signal to the abdominal muscle stimulating electrode after an expiratory duration (0.5 to 5 s); starting outputting the phrenic nerve stimulating signal to the diaphragm stimulating electrode after an end-expiratory pause duration (which is determined by the respiratory frequency, the inspiratory duration, the end-inspiratory pause duration, and the expiratory duration) to enter a next respiratory cycle, and circulating the above process as such until the electrical stimulation duration (1 to 30 min) is reached. It can be seen that, based on the pre-stored configuration data, the method according to this example is able to achieve electrical stimulation respiratory assist under the user configuration, that is, the user inputs the configuration data through an operation interface or other ways, and the electrical stimulation assisted respiratory process is performed using the configuration data.

Figure 2:
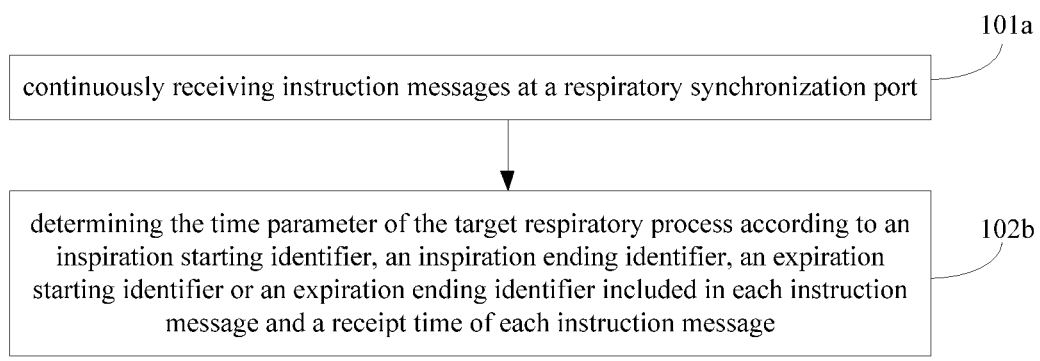
FIG. 2 is a flow chart showing the acquisition of a time parameter of a target respiratory process according to an embodiment of the present disclosure.

As an example where the time parameter of the target respiratory process is derived from the electrical signal collected from the actual respiratory process, FIG. 2 shows a specific flow chart for acquiring the time parameter of the target respiratory process. Referring to FIG. 2, the above step 101 of acquiring a time parameter of a target respiratory process in this example specifically includes:

step 101*a*: continuously receiving instruction messages at a respiratory synchronization port;

step 101*b*: determining the time parameter of the target respiratory process according to an inspiration starting identifier, an inspiration ending identifier, an expiration starting identifier or an expiration ending identifier included in each instruction message and a receipt time of each instruction message.

It is to be understood that, the above instruction message may be generated by an external device, such as by a head-mounted breathing detector through detecting breathing conditions of a wearer, and transmitted to the above respiratory synchronization port via a data connection. As an example, the above instruction message may specifically be 4-byte data. The first four bits of 8-bit data of a header byte contain the inspiration starting identifier (0b1100), the inspiration ending identifier (0b0011), the expiration starting identifier (0b1010) or the expiration ending identifier (0b0101), the fifth and sixth bits are used to indicate a length of the instruction message (for example, 0b11 means there are 3 bytes after the header byte), the seventh bit is left blank, and the eighth bit is used as a parity digit.

Therefore, the above steps 101*a*, 101*b* and 102 constitute the electrical stimulation assisted respiratory process controlled by the respiratory synchronization port, specifically including: determining a receipt time of an instruction message received at the respiratory synchronization port as a start time of a next inspiration (i.e., the time parameter of the target respiratory process acquired at this time) when the instruction message includes the inspiration starting identifier, and outputting the phrenic nerve stimulating signal at the start time of the next inspiration; determining a receipt time of an instruction message received at the respiratory synchronization port as an end time of the current inspiration (i.e., the time parameter of the target respiratory process acquired at this time) when the instruction message includes the inspiration ending identifier, and stopping outputting the phrenic nerve stimulating signal at the end time of the current inspiration; determining a receipt time of an instruction message received at the respiratory synchronization port as a start time of the next expiration (i.e., the time parameter of the target respiratory process acquired at this time) when the instruction message includes the expiration starting identifier, and starting outputting the abdominal muscle stimulating signal at the start time of the next expiration; determining a receipt time of an instruction message received at the respiratory synchronization port as an end time of the current expiration (i.e., the time parameter of the target respiratory process acquired at this time) when the instruction message includes the expiration ending identifier, and stopping outputting the abdominal muscle stimulating signal at the end time of the current expiration. It is understandable from the above description that the above steps 101a, 101b and 102 are not performed in a strict chronological order.

It can be seen that, based on the above steps 101a and 101b, the method according to this example is able to cooperate with a respiratory detecting device to realize the synchronization with the actual respiratory process, or cooperate with an external controller to realize external control of the electrical stimulation assisted respiration, thereby providing the user with much more functional modes. Moreover, the method according to this example is able to cooperate with other devices to achieve a high expansibility and optimize user experience.

Further, on the basis of the method according to this example, the step 101 of acquiring a time parameter of a target respiratory process may further include the following step not shown in FIG. 2:

step 101c: acquiring the time parameter of the target respiratory process from pre-stored configuration data when the time parameter of the target respiratory process is un-obtainable from the instruction message.

Based on the above step 101c, the method according to this example is able to alleviate abnormal outputs caused by data missing or data errors. For example, when the instruction message received at the above respiratory synchronization port includes the inspiration starting identifier, although the phrenic nerve stimulating signal can be output directly based on the acquired start time of the next inspiration, the inspiratory duration corresponding to the duration of the phrenic nerve stimulating signal is a missing time parameter. In step 101c, the inspiratory duration (0.5 to 5 s) may be acquired from the pre-stored configuration data, thereby ensuring that the phrenic nerve stimulating signal will not last too long to cause abnormalities.

Moreover, based on the above step 101c, the method according to this example may automatically acquire the time parameter of the target respiratory process from the pre-stored configuration data to perform the electrical stimulation assisted respiration when the respiratory synchronization port fails or is abnormal, thereby combining the two working modes, which is helpful to improve the reliability and user experience.

In other aspect, an external diaphragm pacemaker in the related art is typically implemented using a voltage-type circuit including a transformer, which makes the volume of the product larger. To overcome this drawback, the phrenic nerve stimulating signal and/or the abdominal muscle stimulating signal in any method for assisting respiration by electrical stimulation as described above may be generated by a current source circuit controlled by a digital signal. Based on this, a processing circuit of the digital signal and the current source circuit both can be implemented in a smaller volume using an integrated chip and/or circuit board, thereby helping to reduce the product volume and the manufacturing costs.

In addition, on the basis of any method for assisting respiration by electrical stimulation as described above, the following step which is not shown in the drawings may be further included:

step 103: detecting an output current of the phrenic nerve stimulating signal and/or that of the abdominal muscle stimulating signal; and generating an electrode detaching indication signal when the output current of the phrenic nerve stimulating signal and/or that of the abdominal muscle stimulating signal are/is lower than a preset value.

Based on this, the method according to this example is able to detect the size of the output current, effectively detect an electrode detaching situation utilizing a principle that body resistance is much smaller than air resistance (i.e., when the electrode is detached, resistance between a positive electrode and a negative electrode is mainly generated by air, and thus the current has an upper limit, based on which the preset value can be predetermined), and further perform a corresponding action for the electrode detaching situation, which is helpful to improve reliability and user experience. For example, the electrode detaching indication signal may be connected to an electrode detaching indicator to alert the user that the electrode is abnormal. Moreover, the electrode detaching indication signal may be connected to a main controller to stop outputting the electrical stimulation signal.

Figure 3:
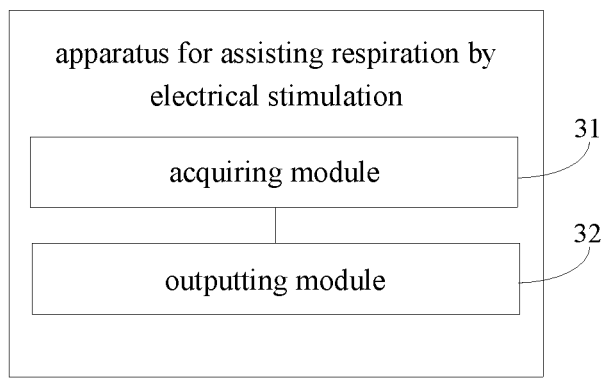
FIG. 3 is a block diagram of an apparatus for assisting respiration by electrical stimulation according to an embodiment of the present disclosure.

Based on the same inventive concept, FIG. 3 shows a block diagram of an apparatus for assisting respiration by electrical stimulation according to an embodiment of the present disclosure. Referring to FIG. 3, the apparatus includes:

an acquiring module 31, configured to acquire a time parameter of a target respiratory process; and an outputting module 32, configured to output a phrenic nerve stimulating signal to a diaphragm stimulating electrode within a time period corresponding to inspiration and output an abdominal muscle stimulating signal to an abdominal muscle stimulating electrode within a time period corresponding to expiration, according to the time parameter of the target respiratory process acquired by the acquiring module 31.

It should be illustrated that, the apparatus for assisting respiration by electrical stimulation according to embodiments of the present disclosure may specifically be any medical apparatus and instrument having a respiratory assisting function, such as a respirator, an external pacemaker, a respiratory rehabilitation therapeutic instrument, etc. It is to be understood that, various components of the apparatus according to embodiments of the present disclosure may be implemented in hardware, software modules running on one or more processors, or a combination thereof. It will be appreciated to those skilled in the art that a microprocessor or a digital signal processor (DSP) may be used in practice to implement some or all of the functions of some or all of the components of the apparatus for assisting respiration by electrical stimulation according to embodiments of the present disclosure. The present disclosure may be implemented as a device or apparatus program (such as a computer program and a computer program product) for performing part or all of the operations described herein. Such a program for implementing the present disclosure may be stored in a computer-readable medium or may be in the form of one or more signals. Such signals may be downloaded from an Internet website, or provided on carrier signals, or provided in any other form.

It is to be understood that, as an example of effects of outputting the phrenic nerve stimulating signal to the diaphragm stimulating electrode within the time period corresponding to the inspiration, user's diaphragm may contract under the stimulation of the phrenic nerve stimulating signal of the diaphragm stimulating electrode, thereby increasing the user's inspiratory tidal volume. As an example of effects of outputting the abdominal muscle stimulating signal to the abdominal muscle stimulating electrode within the time period corresponding to the expiration, user's abdominal muscle may contract under the stimulation of the abdominal muscle stimulating signal of the abdominal muscle stimulating electrode, thereby increasing peak expiratory flow or peak cough flow.

It can be seen that, based on the acquisition of the time parameter of the target respiratory process, the apparatus according to embodiments of the present disclosure applies the electrical stimulations to the diaphragm and the abdominal muscle respectively in accordance with the target respiratory process, thereby making the electrical stimulations on the diaphragm and the abdominal muscle coordinated with each other. Under the case that the target respiratory process sufficiently matches an actual respiratory process, the apparatus according to embodiments of the present disclosure is able to achieve the respiratory assisting electrical stimulation highly synchronized with user's respiratory process, which is not only more beneficial to improving user's spontaneous breathing ability and coughing ability, but also beneficial to increasing the comfortable sensation of the user.

In the function of the above acquiring module 31, it is to be understood that, in order to assist respiration by electrical stimulation, it needs to synchronize the electrical stimulation with the actual respiratory process. Therefore, in order to determine a timing sequence of electrical stimulation signals, it needs to determine the time parameter of the target respiratory process from the target respiratory process before the application of the electrical stimulation, i.e., the time parameter of the target respiratory process specifically refers to a parameter for determining the timing sequence of the electrical stimulation signal. Specifically, the time parameter of the target respiratory process acquired at any time may include any one or more of a start time of a first inspiration, a start time of a first expiration, a start time of a next inspiration, a start time of a next expiration, an end time of the current inspiration, an end time of the current expiration, as well as a respiratory cycle, a respiratory frequency, an inspiratory duration, an end-inspiratory pause duration, and an expiratory duration when the target respiratory process is periodic, which may be selected by those skilled in the art according to actual needs (it is unnecessary to include all the parameters with a conversion relationship). As an example for the selection with a minimum requirement, the time parameter acquired when the phrenic nerve stimulating signal or the abdominal muscle stimulating signal is not output should be at least sufficient to determine a start time of the next phrenic nerve stimulating signal or abdominal muscle stimulating signal to be output, while the time parameter acquired when the phrenic nerve stimulating signal or the abdominal muscle stimulating signal is being output should be at least sufficient to determine an end time of the current output phrenic nerve stimulating signal or abdominal muscle stimulating signal.

It is also to be understood that, after the desired time parameter of the target respiratory process is acquired at any time, at least the start time of the phrenic nerve stimulating signal or the abdominal muscle stimulating signal to be output or the end time of the phrenic nerve stimulating signal or the abdominal muscle stimulating signal being outputted can be determined, such that the apparatus according to embodiments of the present disclosure is able to apply the electrical stimulations in harmony with the actual respiratory process in a configured manner. Of course, the time parameter of the target respiratory process may be derived from pre-stored configuration data or from an electrical signal collected from the actual respiratory process.

As a specific example where the time parameter of the target respiratory process may be derived from the pre-stored configuration data, the workflow of the above acquiring module 31 may specifically include: pre-configuring the target respiratory process as a periodic respiratory process, and acquiring the time parameter thereof, specifically including: the inspiratory duration (0.5 to 5 s), the end-inspiratory pause duration (0 to 2 s), the expiratory duration (0.5 to 5 s), the respiratory frequency (2-25 times per minute), an electrical stimulation duration (1-30 min) and a start time (determined by a key action of the user). Thereby, the workflow of the above outputting module 32 specifically includes the following processes: outputting the phrenic nerve stimulating signal (a current signal) to the diaphragm stimulating electrode at a start time, in which the specific parameter of the phrenic nerve stimulating signal may be pre-configured, including a current intensity ranging from 0 to 100 mA, a pulse frequency ranging from 20 to 100 Hz, or a pulse width ranging from 100 to 500 us; stopping outputting the phrenic nerve stimulating signal to the diaphragm stimulating electrode after an inspiratory duration (0.5 to 5 s) from the start time; stating outputting the abdominal muscle stimulating signal to the abdominal muscle stimulating electrode after an end-inspiratory pause duration (0 to 2 s); stopping outputting the abdominal muscle stimulating signal to the abdominal muscle stimulating electrode after an expiratory duration (0.5 to 5 s); starting outputting the phrenic nerve stimulating signal to the diaphragm stimulating electrode after an end-expiratory pause duration (which is determined by the respiratory frequency, the inspiratory duration, the end-inspiratory pause duration, and the expiratory duration) to enter a next respiratory cycle, and circulating the above process as such until the electrical stimulation duration (1 to 30 min) is reached. It can be seen that, based on the pre-stored configuration data, the apparatus according to this example is able to achieve electrical stimulation respiratory assist under the user configuration, that is, the user inputs the configuration data through an operation interface or other ways, and the electrical stimulation assisted respiratory process is performed using the configuration data.

As a example where the time parameter of the target respiratory process is derived from the electrical signal collected from the actual respiratory process, the above acquiring module 31 specifically includes:

a receiving unit, configured to continuously receive instruction messages at a respiratory synchronization port; and a determining unit, configured to determine the time parameter of the target respiratory process according to an inspiration starting identifier, an inspiration ending identifier, an expiration starting identifier or an expiration ending identifier included in each instruction message and a receipt time of each instruction message.

It is to be understood that, the above instruction message may be generated by an external device, such as by a head-mounted breathing detector through detecting breathing conditions of a wearer, and transmitted to the above respiratory synchronization port via a data connection. As an example, the above instruction message may specifically be 4-byte data. The first four bits of 8-bit data of a header byte contain the inspiration starting identifier (0b1100), the inspiration ending identifier (0b0011), the expiration starting identifier (0b1010) or the expiration ending identifier (0b0101), the fifth and sixth bits are used to indicate a length of the instruction message (for example, 0b11 means there are 3 bytes after the header byte), the seventh bit is left blank, and the eighth bit is used as a parity digit.

Therefore, the above receiving unit, the determining unit and the outputting unit 32 together realizes the electrical stimulation assisted respiration controlled by the respiratory synchronization port, and the specific processes includes: determining a receipt time of an instruction message received at the respiratory synchronization port as a start time of a next inspiration (i.e., the time parameter of the target respiratory process acquired at this time) when the instruction message includes the inspiration starting identifier, and starting outputting the phrenic nerve stimulating signal at the start time of the next inspiration; determining a receipt time of an instruction message received at the respiratory synchronization port as an end time of the current inspiration (i.e., the time parameter of the target respiratory process acquired at this time) when the instruction message includes the inspiration ending identifier, and stopping outputting the phrenic nerve stimulating signal at the end time of the current inspiration; determining a receipt time of an instruction message received at the respiratory synchronization port as a start time of the next expiration (i.e., the time parameter of the target respiratory process acquired at this time) when the instruction message includes the expiration starting identifier, and starting outputting the abdominal muscle stimulating signal at the start time of the next expiration; determining a receipt time of an instruction message received at the respiratory synchronization port as an end time of the current expiration (i.e., the time parameter of the target respiratory process acquired at this time) when the instruction message includes the expiration ending identifier, and stopping outputting the abdominal muscle stimulating signal at the end time of the current expiration.

It can be seen that, based on the above receiving unit and the determining unit, the apparatus according to this example of the present disclosure is able to cooperate with a respiratory detecting device to realize the synchronization with the actual respiratory process, or cooperate with an external controller to realize external control of the electrical stimulation assisted respiration, thereby providing the user with much more functional modes. Moreover, the apparatus according to this example of the present disclosure is able to cooperate with other devices to achieve a high expansibility and optimize user experience.

Further, on the basis of the apparatus of this example, the above acquiring module 31 may further include: an acquiring unit, configured to acquire the time parameter of the target respiratory process from pre-stored configuration data when the time parameter of the target respiratory process is un-obtainable from the instruction message.

Based on the above acquiring unit, the apparatus according to this example is able to alleviate abnormal outputs caused by data missing or data errors. For example, when the instruction message received at the above respiratory synchronization port includes a starting identifier for stimulating diaphragm, although the phrenic nerve stimulating signal can be output directly based on the acquired start time of the next inspiration, the inspiratory duration corresponding to the duration of the phrenic nerve stimulating signal is a missing time parameter. In step 101c, the inspiratory duration (0.5 to 5 s) may be acquired from the pre-stored configuration data, thereby ensuring that the phrenic nerve stimulating signal will not last too long to cause abnormalities.

Moreover, based on the above acquiring unit, the apparatus according to this example may automatically acquire the time parameter of the target respiratory process from the pre-stored configuration data to perform the electrical stimulation assisted respiration when the respiratory synchronization port fails or is abnormal, thereby combining the two working modes, which is helpful to improve the reliability and user experience.

In other aspect, an external diaphragm pacemaker in the related art is typically implemented using a voltage-type circuit including a transformer, which makes the volume of the product larger. To overcome this drawback, the outputting module 32 in any apparatus for assisting respiration by electrical stimulation as described above may include a current source circuit controlled by a digital signal, and the phrenic nerve stimulating signal and/or the abdominal muscle stimulating signal are/is generated by the current source circuit controlled by the digital signal. Based on this, a processing circuit of the digital signal and the current source circuit both can be implemented in a smaller volume using an integrated chip and/or circuit board, thereby helping to reduce the product volume and manufacturing costs.

In addition, on the basis of any apparatus for assisting respiration by electrical stimulation as described above, the following structure which is not shown in the drawings may be further included: a detecting module 33, configured to detect an output current of the phrenic nerve stimulating signal and/or that of the abdominal muscle stimulating signal and generate an electrode detaching indication signal when the output current of the phrenic nerve stimulating signal and/or that of the abdominal muscle stimulating signal are/is lower than a preset value.

Based on this, the apparatus according to this example is able to detect the size of the output current, effectively detect an electrode detaching situation utilizing a principle that body resistance is much smaller than air resistance (i.e., when the electrode is detached, resistance between a positive electrode and a negative electrode is mainly generated by air, and thus the current has an upper limit, based on which the preset value can be predetermined), and further perform a corresponding action for the electrode detaching situation, which is helpful to improve reliability and user experience. For example, the electrode detaching indication signal may be connected to an electrode detaching indicator to alert the user that the electrode is abnormal. Moreover, the electrode detaching indication signal may be connected to a main controller to stop outputting the electrical stimulation signal.

Figure 4:
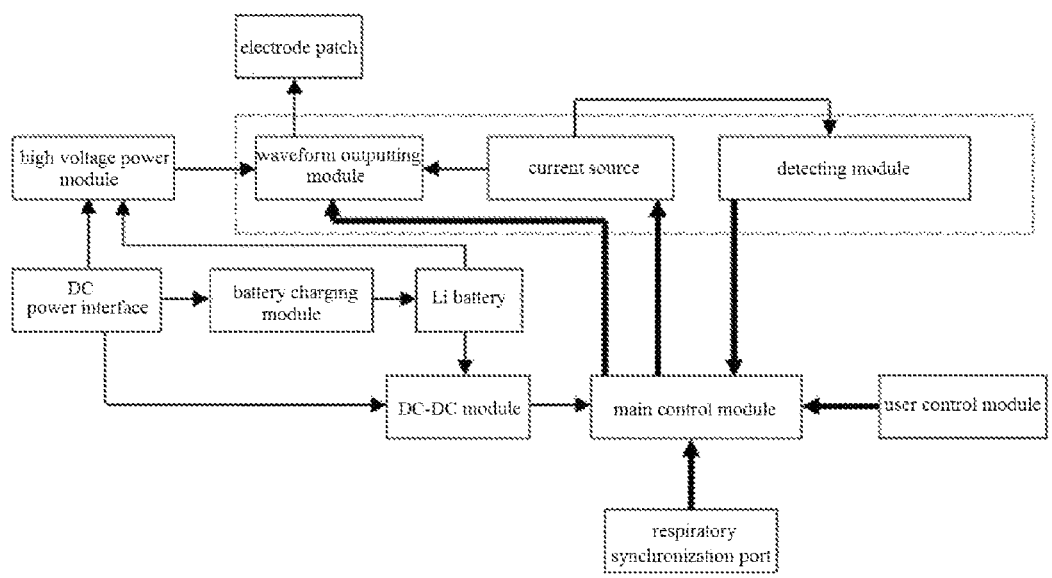
FIG. 4 is a block diagram of an apparatus for assisting respiration by electrical stimulation according to an embodiment of the present disclosure.

As a more specific example, FIG. 4 illustrates a block diagram of an apparatus for assisting respiration by electrical stimulation according to an embodiment of the present disclosure. Referring to FIG. 4, the apparatus of this example specifically includes a main control module, a user control module, a lithium battery, a battery charging module, a DC power interface, a current source, a high voltage power module, a DC-DC module, a waveform outputting module, an electrode patch, the above-described detecting module and respiratory synchronization port. Therefore, the apparatus according to this example may be powered by either an external DC power supply or the internal lithium battery. Specifically, the DC power interface may be connected to an external power adapter to transmit power to the battery charging module, the high voltage power module and the DC-DC module. The main control module is mainly formed by a processor to implement all logic operations and logic processing in the electrical stimulation assisted respiratory function. When the electrical stimulation signal to be output is determined by the main control module, a corresponding control signal is transmitted to the current source and the waveform outputting module to form a corresponding phrenic nerve stimulating signal or abdominal muscle stimulating signal, which is output by the electrode patch. The above detecting module is directly connected with the main control module to implement the generation of the electrode detaching indication signal. The respiratory synchronization port is also connected with the main control module to receive the above-mentioned instruction messages based on a serial communication mode. In addition, the user control module is connected with the main control module, and mainly used as a user input/output device to interact with the user and write information input by the user into an internal storage via the main control module.

In summary, based on the acquisition of the time parameter of the target respiratory process, the method and apparatus according to embodiments of the present disclosure applies the electrical stimulations to the diaphragm and the abdominal muscle respectively in accordance with the target respiratory process, thereby making the electrical stimulations on the diaphragm and the abdominal muscle coordinated with each other. Under the case that the target respiratory process sufficiently matches an actual respiratory process, the present disclosure is able to achieve the respiratory assisting electrical stimulation highly synchronized with user's respiratory process, which is not only more beneficial to improving user's spontaneous breathing ability and coughing ability, but also beneficial to increasing the comfortable sensation of the user.

Embodiments of the present disclosure further provide a device, including: one or more processors; a memory; and one or more procedures stored in the memory, wherein the one or more procedures, when executed by the one or more processors, cause the one or more processors to perform the method for assisting respiration by electrical stimulation as described in embodiments hereinbefore.

Embodiments of the present disclosure further provide a nonvolatile computer storage medium having stored therein one or more procedures that, when executed by a device, cause the device to perform a method for assisting respiration by electrical stimulation as described in embodiments hereinbefore.

In addition, other configurations and functions of the method, apparatus and device for assisting respiration by electrical stimulation and the nonvolatile computer storage medium are known to those skilled in the art, and will not elaborated herein.

Reference throughout this specification to "an embodiment", "some embodiments", "one embodiment", "an example", "a specific example", or "some examples", means that a particular feature, structure, material, or characteristic described in connection with the embodiment or example is included in at least one embodiment or example of the present disclosure. Thus, the appearances of the phrases such as "in some embodiments", "in one embodiment", "in an embodiment", "in an example", "in a specific example", or "in some examples", in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that various changes, modifications, alternatives and variations can be made to these embodiments without departing from the principles and spirits of the present disclosure, and the scope of which is limited by the claims and their equivalents.

What is claimed is:

1. A method comprising:
acquiring a time parameter of a target respiratory process;
outputting a phrenic nerve stimulating signal to a diaphragm stimulating electrode within a time period corresponding to inspiration and outputting an abdominal muscle stimulating signal to an abdominal muscle stimulating electrode within a time period corresponding to expiration, according to the time parameter of the target respiratory process;
detecting an output current of the phrenic nerve stimulating signal and that of the abdominal muscle stimulating signal; and
generating an electrode detaching indication signal when the output current of at least one of the phrenic nerve stimulating signal and the abdominal muscle stimulating signal is lower than a preset value.

2. The method according to claim 1, wherein acquiring a time parameter of a target respiratory process comprises:
continuously receiving instruction messages at a respiratory synchronization port; and
determining the time parameter of the target respiratory process according to an inspiration starting identifier, an inspiration ending identifier, an expiration starting identifier or an expiration ending identifier included in each instruction message and a receipt time of each instruction message.

3. The method according to claim 1, wherein acquiring a time parameter of a target respiratory process further comprises:
acquiring the time parameter of the target respiratory process from pre-stored configuration data when the time parameter of the target respiratory process is un-obtainable from an instruction message at a respiratory synchronization port.

4. The method according to claim 1, wherein the phrenic nerve stimulating signal and the abdominal muscle stimulating signal are generated by a current source circuit controlled by a digital signal.

5. A device, comprising:
one or more processors;
a memory;
one or more procedures stored in the memory;
a diaphragm stimulating electrode; and
an abdominal muscle stimulating electrode,
wherein the one or more procedures, when executed by the one or more processors, cause the one or more processors to perform a method comprising:
acquiring a time parameter of a target respiratory process;
outputting a phrenic nerve stimulating signal to the diaphragm stimulating electrode within a time period corresponding to inspiration and outputting an abdominal muscle stimulating signal to the abdominal muscle stimulating electrode within a time period corresponding to expiration, according to the time parameter of the target respiratory process;
detecting an output current of the phrenic nerve stimulating signal and that of the abdominal muscle stimulating signal; and generating an electrode detaching indication signal when the output current of at least one of the phrenic nerve stimulating signal and the abdominal muscle stimulating signal is lower than a preset value.

6. The device according to claim 5, wherein acquiring a time parameter of a target respiratory process comprises:
continuously receiving instruction messages at a respiratory synchronization port; and
determining the time parameter of the target respiratory process according to an inspiration starting identifier, an inspiration ending identifier, an expiration starting identifier or an expiration ending identifier included in each instruction message and a receipt time of each instruction message.

7. The device according to claim 5, wherein acquiring a time parameter of a target respiratory process further comprises:
acquiring the time parameter of the target respiratory process from pre-stored configuration data when the time parameter of the target respiratory process is un-obtainable from an instruction message at a respiratory synchronization port.

8. The device according to claim 5, further comprising a current source circuit controlled by a digital signal, configured to generate the phrenic nerve stimulating signal and the abdominal muscle stimulating signal.

9. A nonvolatile computer storage medium having stored therein one or more procedures that, when executed by a device, cause the device to perform a method comprising:
acquiring a time parameter of a target respiratory process;
outputting a phrenic nerve stimulating signal to a diaphragm stimulating electrode within a time period corresponding to inspiration and outputting an abdominal muscle stimulating signal to an abdominal muscle stimulating electrode within a time period corresponding to expiration, according to the time parameter of the target respiratory process;
detecting an output current of the phrenic nerve stimulating signal and that of the abdominal muscle stimulating signal; and
generating an electrode detaching indication signal when the output current of at least one of the phrenic nerve stimulating signal and the abdominal muscle stimulating signal is lower than a preset value.

* * * * *